United States Patent [19]

Walsh

[11] Patent Number: 4,940,576

[45] Date of Patent: Jul. 10, 1990

[54] HAIR CONDITIONING PREPARATION

[75] Inventor: Michael F. Walsh, South Wirral, United Kingdom

[73] Assignee: Conopco, Inc. d/b/a/ Chesebrough-Pond's USA Co., Greenwich, Conn.

[21] Appl. No.: 67,434

[22] Filed: Jun. 26, 1987

Related U.S. Application Data

[63] Continuation of Ser. No. 510,117, Jul. 1, 1983, abandoned.

[30] Foreign Application Priority Data

Jul. 7, 1982 [GB] United Kingdom ............... 8219673

[51] Int. Cl.$^5$ .......................... A61K 7/06; A61K 7/08
[52] U.S. Cl. ....................................... 424/70; 424/78; 424/80; 424/81
[58] Field of Search .......................... 424/70

[56] References Cited

U.S. PATENT DOCUMENTS

| | | | |
|---|---|---|---|
| 3,472,840 | 10/1969 | Stone et al. | 260/331 |
| 3,761,417 | 9/1973 | Parran | 252/106 |
| 3,912,808 | 10/1975 | Sokol | 424/71 |
| 3,986,825 | 10/1976 | Sokol | 424/70 |
| 3,996,146 | 12/1976 | Tarasov et al. | 424/70 |
| 4,027,008 | 5/1977 | Sokol | 424/62 |
| 4,027,020 | 5/1977 | Green et al. | 424/248.56 |
| 4,273,760 | 6/1981 | Koehler et al. | 424/70 |
| 4,402,936 | 9/1983 | Okumura et al. | 424/70 |
| 4,445,521 | 5/1984 | Grollier et al. | 424/70 |

FOREIGN PATENT DOCUMENTS

| | | | |
|---|---|---|---|
| 0034190 | 8/1981 | European Pat. Off. | 424/70 |
| 2419758 | 12/1979 | France | 424/70 |
| 0157841 | 5/1978 | Japan | 424/70 |
| 54-35222 | 3/1979 | Japan | 424/70 |
| 2021411 | 12/1979 | United Kingdom | 424/70 |
| 2044615 | 10/1980 | United Kingdom | 424/70 |
| 2057261 | 4/1981 | United Kingdom | 424/70 |
| 1603321 | 10/1981 | United Kingdom | 424/70 |

OTHER PUBLICATIONS

Japanese Patent 54 35222, English Language Abstract from Pat. Abs. of Japan, Section C, vol. 3, No. 59 (C-46), May 19, 1979, p. 142C46.

"Clear Hair Rinses", L. R. Smith et al., Soap, Cosm, Chem. Specialties, 4/1977, pp. 50 and 52.

"Aggregation Processes in Solution", ed. Jones et al., 1983.

"Aggregation Processes in Solution", edited by E. Wyn-Jones and J. Gormally, Elsevier Scientific Publishing Company, 1983.

Primary Examiner—Dale R. Ore
Attorney, Agent, or Firm—Milton L. Honig

[57] ABSTRACT

The invention relates to an aqueous clear single-phase liquid hair rinse conditioner. On dilution of the conditioner during use there is deposited on the hair a lyotropic liquid crystal phase formed by interaction between an ionised polymer and an ionic surfactant of opposite charge. There is also present in the composition a clarifying agent in order to maintain the composition in the form of a clear single-phase solution prior to dilution. The polymer-surfactant complex in the form of a liquid crystal phase deposited from the hair conditioner of the invention is more effective to improve the ease of wet combing of the hair than a complex not in the form of a liquid crystal.

1 Claim, No Drawings

HAIR CONDITIONING PREPARATION

This is a continuation of application Ser. No. 510,117, filed July 1, 1983.

This invention relates to hair conditioning preparations and in particular to conditioning hair rinses which are sometimes simply called hair rinses. These products are intended to be applied to wet hair following shampooing, and after rinsing off they leave the hair in an improved condition. In particular this treatment makes the hair more manageable and improves especially the wet-combability of the hair. Although such products may be formulated as a simple aqueous solution of a cationic quaternary ammonium compound, for example cetyltrimethylammonium chloride, it has been usual to combine with the cationic ingredient a fatty material such as a fatty alcohol, e.g. stearyl alcohol, so as to form a cream and the product is known as a cream rinse-conditioner. The conditioning properties are enhanced by the inclusion of the fatty material but the product can no longer be formulated in a clear water-white form. It is also known to formulate clear hair rinse conditioners based on the combination of a quaternary ammonium compound and a cationic polymer. These products, however, have limited effectiveness. A number of formulae for clear rinse-conditioners are proposed in an article by L. R. Smith & M. Weinstein entitled "Clear Hair Rinses" published in Soap/Cosmetics/Chemical Specialties, April 1977, pages 50 and 52.

It is an object of the invention to provide an improved clear hair rinse conditioner.

According to the present invention there is provided an aqueous clear single-phase liquid hair rinse conditioner composition comprising a water-soluble ionised polymer and an ionic surfactant of opposite charge which interact with each other to form a complex which separates out upon dilution of the composition as a lyotropic liquid crystal phase, the composition also comprising a clarifying agent to maintain the composition in the form of a clear single-phase solution prior to dilution, the amount of the ionic surfactant being 0.9 to 2.0 S moles where S Moles is the amount of the surfactant required to completely neutralise the charges on the polymer, the combined weight of the ionised polymer and the ionic surfactant being 0.1 to 5% by weight of the composition, and said composition comprising not more than 5% by weight of neutral surfactant.

The clear hair rinse conditioner of the invention has as an essential and novel characteristic the feature that the complex between the ionised polymer and the ionic surfactant that separates out upon dilution of the product with water is in the form of a lyotropic liquid crystal (referred to hereinafter simply as a liquid crystal). It has been discovered that complexes which separate out as a liquid crystal phase are superior in improving the wet combing properties of hair compared to those complexes which do not separate out as a liquid crystal.

It is believed that a complex between an ionised polymer and an ionic surfactant of opposite charge in the form of a liquid crystal has not previously been reported in the literature. Applicant has found that ionised polymers which have regions having a charge density of at least 0.006 and a degree of ionic character (as herein defined) of at least 0.7 can interact electrostatically with an oppositely charged surfactant to form a complex in the form of a liquid crystal. The polymer may be a copolymer having the above characteristics or it may be a random copolymer having charged regions which are block in nature and which regions have the above characteristics. Charge density as that term is used herein refers to the ratio of the number of charges on a polymer unit to the molecular weight of said polymer unit. By the degree of ionic character is meant the ratio of the number of ionic groups of the polymer region to the number of polymer units of which the polymer region is composed. In the case of a charged polysaccharide the degree of ionic character is more commonly known as its degree of substitution which is the number of charged substituent groups that are present per saccharide unit. Preferably the polymer as a whole has a charge density of at least 0.006 and a degree of ionic character of at least 0.7.

The polymer is preferably a cationic polymer. A particularly suitable cationic polymer is poly (dimethyldiallylammonium chloride): this has a charge density of about 0.008 and a degree of ionic character of 1.0. This polymer has the CTFA designation Quaternium 40 and is available commercially as a 40% aqueous solution under the trade name MERQUAT 100 from the Merck Chemical Division of Merck & Co. Inc., USA. Another suitable cationic polymer is poly(dimethylbutenyl ammonium chloride)-α,ω-bis(triethanolammonium chloride) which is commercially available under the trade name ONAMER M from the Onyx Chemical Co., USA and is described in U.S. Pat. No. 4,027,020; the polymer has a cationic charge density of 0:01 and a degree of ionic character of 1.0. The CTFA designation of this polymer is Quaternium 57. Other suitable cationic polymers are poly(dipropyldiallylammonium chloride), poly(methyl-beta-propaniodiallylammonium choride), poly(diallylpiperidinium chloride), poly(vinyl pyridinium chloride), quaternised poly(vinyl alcohol) and quaternised poly (dimethylaminoethylmethacrylate), the degree of quaternisation of the respective polymers being such as to impart a charge density of at least 0.006 and a degree of ionic character of at least 0.7. Further suitable cationic polymers are those known as Polymer QR 686, an imidazoline acetate derivative available from Rohm & Haas, and CARTARETIN K, a crosslinked polyamidepolyamine available from Sandoz. Non-quaternary polymers may also be used such as poly (N-vinyl pyrollidone), poly(dimethylaminoethylmethacrylate), poly(vinyl pyridine) and poly(ethyleneimine) protonated under such conditions of pH to give a charge density of at least 0.006 and a degree of ionic character of at least 0.7.

Copolymers of the above with other monomers such as, for example, acrylamide, diacetone acrylamide and styrene may also be used provided the charge density of the copolymer is at least 0.006 and the degree of ionic character is at least 0.7.

A suitable anionic polymer is polyacrylic acid at a sufficient pH to ionize at least 70% of the acid groups so as to give the polymer a degree of ionic character of at least 0.7. Other suitable polymer types are poly (methacrylic acid), poly(styrene sulphonate) and copolymers of ethylene and maleic acid.

The ionic polymer employed in this invention will usually have a molecular weight in the range 1,000 to 6,000,000.

A further essential component of the rinse conditioner of the invention is the ionic surfactant having a charge opposite to that on the ionised polymer. Thus, if the polymer is a cationic polymer, the surfactant is an anionic surfactant. The surfactant, because it has a charge opposite to that of the polymer, reacts with the polymer to form a polymer-surfactant complex. The formation of complexes between polymers and surfactants of opposite charge is well known. However, in the rinse conditioner product of this invention it is an essential requirement that the complex which separates out on dilution of the product with water should be in the form of a lyotropic liquid crystal. Lyotropic liquid crystals are well known and a recent book describing them is entitled "Aggregation Processes in Solution" edited by E. Wyn-Jones and J. Gormally published by Elsevier Scientific Publishing Company, Amsterdam-Oxford-N.Y. 1983, and particular reference is made to Chapter 7 entitled "Lyotropic Liquid Crystals". It is believed, however, that the formation of a lyotropic liquid crystal by electrostatic interaction between an ionised polymer and an oppositely charged ionic surfactant has not previously been reported. In the formation of the liquid crystal the polymer and surfactant molecules will generally form into rods which then arrange themselves into an hexagonal array thus producing an hexagonal liquid crystal. However, as will be explained hereinafter, the complex can be in the form of a liquid crystal phase having a lamellar structure. A product comprising or leading to the formation of polymer-surfactant complex which is not in the form of a liquid crystal phase gives an inferior result, as will be illustrated hereinafter.

Suitable anionic surfactants types from which surfactants for use in the hair conditioner of the invention may be chosen are the alkyl sulphates, eg sodium lauryl sulphate; alkyl ether sulphates, eg sodium lauryl ether (2EO) sulphate or sodium lauryl ether (3EO) sulphate; alkyl carboxylates, eg potassium laurate; aryl alkyl sulphonates, eg sodium dodecyl benzene sulphonate; dialkyl sulphosuccinates, eg sodium di-octyl sulphosuccinate; organic phosphate esters, eg sodium oleyl ether phosphates; dialkyl sulphosuccinamates, eg sodium di-N-lauryl sulphosuccinamate; acyl sarcosinates, eg sodium N-lauroyl sarcosinate; alkyl taurates, eg sodium N-methyl-N-oleyl taurate; and alkyl isethionates.

Examples of suitable types of cationic surfactants for use in conjunction with the anionic polymers are cetyltrimethyl ammonium salts, stearyldimethyl ammonium salts, dimethyldialkyl ammonium salts, polyethoxylated quaternary ammonium salts, cetylpyridinium chloride, oleyldimethylbenzyl ammonium halides, methyl bis-(2-hydroxyethyl)oleyl ammonium chloride, and oleyl ammonium chloride. Preferred ammonium salts are the chloride and bromide salts. Other surfactants which under appropriate pH conditions have cationic character can also be used, for example amidoamine oxide derivatives of lauric acid and alkyl betaines.

It is required that the surfactant be one which results in a complex with the ionic polymer which is in the form of a liquid crystal. Generally for surfactants containing an alkyl chain this chain should have more than 8 carbon atoms. For the lauryl ether sulphates the ethylene oxide content should be less than $(EO)_{12}$. For alkyl ether sulphates having an alkyl group of more than 12 carbon atoms, an ethylene oxide content of more than $(EO)_{12}$ may be appropriate. It is a simple matter to test whether a particular combination of ionic polymer and oppositely charged surfactant will result in a complex which exists as a liquid crystal phase. One has merely to form an aqueous mixture of the two ingredients in such proportions as to give maximum precipitation and then examine the complex formed using a polarising microscope to establish the presence of a liquid crystal phase. Liquid crystals when viewed under a polarising microscopic display distinct optical textures which are characteristic of such structures.

While the proportion of the ionic surfactant in the hair conditioner composition in relation to the ionic polymer should be at least sufficient to be capable of forming the desired complex, it should not be present in substantial excess. The amount of the surfactant should be in the range 0.9 to 2.0 S moles where S moles is the amount of the surfactant necessary to result in complete neutralisation of the charges on the polymer. In proportions of polymer and surfactant giving maximum precipitation of the complex the value of S is unity or about unity. The value of S can also be readily calculated from the charge density of the polymer and the amount of the polymer in the composition. Applicant has found that the presence of surfactant in an amount greater than 2.0 S moles reduces the efficacy of the hair conditioner. Preferably the amount of surfactant is from 0.9 to 1.5 S moles, more preferably 0.9 to 1.2 S moles.

The combined weight of the polymer and surfactant is from about 0.1% to 5%, preferably 0.2% to 4%, by weight of the conditioner composition.

The complex formed between the ionic polymer and the surfactant is water-insoluble and for this reason the composition of the invention includes a clarifying agent to maintain the composition in the form of a clear single phase solution prior to dilution. In order to produce an optically clear single-phase liquid it is necessary to dissociate or dissolve the complex and the clarifying agent is included for this purpose. The composition can be rendered clear by the inclusion of certain electrolytes and/or water-soluble organic co-solvents. Certain simple salts are effective to dissociate the complex by weakening the electrolytic interactions between the polymer and the surfactant. Suitable salts include the chlorides, bromides and nitrates of the alkali metals, alkaline-earth metals and ammonium (including substituted ammonium salts). Specific examples of suitable salts are sodium chloride, sodium bromide, sodium nitrate, potassium chloride, potassium bromide, calcium chloride, magnesium chloride and ammonium chloride. While the action of the electrolyte alone in some cases is effective to produce a clear single-phase product, in other cases, particularly where the polymer and surfactant interact strongly, electrolyte alone may not result in a clear solution and it is then necessary to include an organic co-solvent to give a completely clear product.

Examples of suitable organic co-solvents which can be used for producing the clear single-phase product of the invention are the water-soluble alkyl alcohols of which propan-1-ol is preferred. However other $C_1$-$C_6$ alkyl alcohols, for example methanol and ethanol are effective although the use of a greater amount of these alcohols may be required. Other water-soluble co-solvents that are helpful in solubilising the polymer-surfactant complex to give a clear product are benzyl alcohol, hexylene glycol, hexan-1,2-diol, 2-butoxy-ethanol, octyne diol, diethylene glycol, tetraethylene glycol, monomethyl ether of diethylene glycol (methyl digol), monoethyl ether of diethylene glycol (ethyl digol) and monobutyl ether of diethylene glycol (butyl digol). Butyl digol is a preferred co-solvent.

In some cases addition of electrolyte alone leads to the formation of a product consisting of two clear layers. In this case the addition of the organic co-solvent is also necessary to give a single-phase product. The use of a combination of electrolyte and co-solvent is also preferable to the use of co-solvent alone since the use of substantial amounts of co-solvent are generally then necessary.

The amount of the electrolyte and/or co-solvent required to form a clear single-phase solution may depend on the amount of the complex present in the rinse conditioner composition and on the strength of the polymer-surfactant intraction. Generally an electrolyte will be required to be used in an amount of from 0.1 to 20% by weight of the rinse conditioner and a co-solvent in an amount of from 0.1 to 90% by weight of the rinse conditioner.

An optional, although preferred, additional component of a rinse conditioner product of this invention is a thickening agent in order to increase the viscosity of the composition. Any suitable nonionic thickener may be used for this purpose, for example neutral polymeric thickeners such as the cellulosic thickeners which include hydroxyethylcellulose, hydroxypropylcellulose, polyacrylamide and polyethylene glycol.

Perfume and colouring agents may also be incorporated into the rinse conditioner.

If a perfume oil is included in the hair rinse conditioner composition of the invention it may be advantageous in order to solubilise the perfume to also incorporate a neutral surfactant, i.e. a surfactant whose molecule bears no charge or net charge. Suitable neutral surfactants are amphoteric surfactants, for example alkyl beta-iminodipropionates, substituted betaines or amine oxides, and non-ionic surfactants, such as polyethylene oxide condensates of alkyl phenols or of aliphatic alcohols, which are well known to those skilled in the art. However, the composition of the invention contains not more than 5%, and preferably less than 3% of neutral surfactant. Amounts of neutral surfactant substantially in excess of 5% by weight of the composition may interfere with the deposition and/or formation of the polymer-surfactant liquid crystal upon dilution of the composition during the rinsing stage and in any case such amounts would be regarded as disadvantageous in tending to cause the rinse conditioner product to foam which is not desirable.

The invention also relates to a method of conditioning hair comprising applying the aqueous hair rinse conditioner of the invention to wet hair and thereafter rinsing the hair with water. In this procedure the rinse conditioner is substantially diluted and this results in the precipitation and deposition of the polymer-surfactant complex onto the hair. Although this complex is substantially neutral it is nevertheless highly functional as a hair conditioner and this is due to its liquid crystal character. This complex is surprisingly more effective than the combination of a cationic surfactant and a cationic polymer.

An additional advantage of the preferred conditioner product of the invention in which the cationic species is polymeric is that it is less irritant to the eyes than conventional rinse conditioners based on cationic surfactants.

The liquid crystal phase formed using products of the invention is normally hexagonal. However, in the presence of certain additives, such as decanol, the hexagonal phase can be transformed into a lamellar liquid crystal phase. A lamellar liquid crystal phase is also produced, without the use of additions, when certain surfactants are employed. This lamellar phase exhibits hair conditioning properties somewhat similar to the preferred hexagonal phase.

The following examples illustrate the invention. Percentages are by weight.

EXAMPLE 1

The following clear single-phase hair rinse conditioner was made.

|  | % |
| --- | --- |
| Merquat 1001[1] | 0.25 |
| Sodium lauryl ether sulphate (3EO)[2] | 0.65 |
| Sodium chloride | 12.0 |
| Propan-1-ol | 6.0 |
| Hydroxyethylcellulose[3] | 0.65 |
| Perfume oil | 0.2 |
| Coco-amido betaine[4] | 0.48 |
| Preservative (formalin) | 0.05 |
| Water (deionised) | to 100.0 | pH 5.0-5.5
[1] poly (dimethydiallylammonium chloride) having an average molecular weight of $10^5$–$10^6$;
[2] the amount of the surfactant is equivalent to 1.0 S where S is the amount of the surfactant required to completely neutralise the charge on the cationic polymer;
[3] to give a viscosity of 600–800 cps at 25° C.;
[4] an amphoteric surfactant to aid solubilisation of the perfume.

The above composition was made in the following way. To the Merquat 100 was added part of the water, with stirring, followed by an aqueous solution of the surfactant. The complex forms as a precipitate and this is dissociated by the addition of the salt and the resulting cloudy solution is rendered clear by the addition of the propanol-1-ol. The perfume, amphoteric surfactant, preservative and a solution of the thickener is the remainder of the water are then added.

The above hair conditioner was compared in a wet combing test with a commercial clear rinse conditioner based on the combination of a cationic surfactant (cetyltrimethylammonium bromide) and a cationic polymer (Polymer JR 400) and also with an opaque cream rinse conditioner based on the combination of a cationic surfactant (cetyltrimethylammonium bromide) and a fatty alcohol (ceto/stearyl alcohol). The wet combing test was carried out in the following manner.

A hair switch (8 g) was washed with a surfactant solution (16% monoethanolamine lauryl sulphate) (MLS) in two stages, this solution being referred to hereafter as the surfactant base. In the first application 0.5 ml of the surfactant base was applied to the wetted hair, the switch lathered for 30 seconds and, after leaving for a further 20 seconds, the hair was rinsed with water. This was repeated but using 0.4 ml of the surfactant base. After rinsing and removing excess water, the hair was combed until free of tangles with a comb which was in association with an instrument which measured the total combing time (TCT). The TCT value after treatment with the surfactant base is T1. The hair switch was then treated with 0.5 ml of the hair conditioner test product which was massaged into the hair for 30 seconds. After leaving for 60 seconds the hair switch was rinsed with water. After removing excess water, the switch was again combed until free of tangles to give a TCT value of T2. The combing time after treatment with the test hair conditioner product expressed as a percentage of that after
treatment with the surfactant base is $$\frac{T2}{T1} \times 100.$$

The procedure was carried out on two other hair switches and the average of the percentage values for the three switches was taken as the wet combing value for the test product. Thus the more effective the product, the lower the wet combing value. A different set of three switches was used for each test product. The wet combing values given in this example and the subsequent examples were all obtained by the same operator. The reproducibility of the wet combing values was found to be ±2 units The results are given in the following table

| Test Product | Wet Combing Value |
| --- | --- |
| Conditioner of Example 1 | 28 |
| Commercial clear conditioner | 38 |
| Commercial opaque conditioner | 30 |

The conditioner of Example 1 was significantly better than the commercial clear conditioner at the 1% level. The results also show that the clear conditioner of the invention is at least equivalent to the commercial opaque conditioner.

The results have been confirmed by an in-vivo evaluation in the hair salon. The product of the invention was judged to be superior at the 5% significance level to the commercial clear conditioner in the ease of wet combing of the hair. Furthermore, the product of the invention was judged to be similar to the commercial opaque conditioner with no significant differences between the various attributes being compared which also included hair gloss, static charge and ease of styling. The product of the invention is considerably less irritant to the eyes than the commercial clear formulation.

EXAMPLE 2

The following clear single-phase hair rinse conditioner was made.

|  | % |
| --- | --- |
| Merquat 100 | 0.25 |
| Sodium lauryl ether sulphate (3EO) | 0.65 |
| Sodium chloride | 12.0 |
| Butyl digol | 3.0 |
| Hydroxyethylcellulose | 0.65 |
| Perfume oil | 0.2 |
| Coco-amido betaine | 0.48 |
| Preservative | 0.05 |
| Water | to 100.0 |

This product gave a wet combing value of 27.

EXAMPLES 3 and 4

The following clear single-phase hair rinse conditioners were made.

|  | Example | |
| --- | --- | --- |
|  | 3 | 4 |
| Merquat 100 | 0.5 | 1.0 |
| Sodium lauryl ether sulphate (3EO) | 1.3 | 2.6 |
| Butyl digol | 2.0 | 2.0 |
| Sodium chloride | 12.0 | 12.0 |
| Water | to 100.0 | to 100.0 |

Examples 3 and 4 gave wet combing values of 29 and 30, respectively.

EXAMPLE 5

The following clear single-phase hair rinse conditioner was prepared.

|  | % |
| --- | --- |
| Cartaretin K[1] | 0.25 |
| Sodium lauryl ether sulphate (3EO)[2] | 0.24 |
| Sodium chloride | 12.00 |
| Butyl digol | 1.00 |
| Water | to 100.00 |

[1] a cationic cross-linked polyamidepolyamine having a charge density of greater than 0.006 and a degree of ionic character greater than 0.7.
[2] the amount of surfactant corresponds to that maximum precipitation of the complex.

This composition gave a wet combing value of 27.

EXAMPLE 6

A clear single-phase hair rinse conditioner was prepared having the following composition.

|  | % |
| --- | --- |
| Polymer QR 686[1] | 0.3 |
| Sodium lauryl ether sulphate (3EO)[2] | 0.9 |
| Sodium chloride | 12.0 |
| Ethyl digol | 0.7 |
| Water | to 100.0 |

[1] a cationic polymeric imidazoline acetate derivative having a charge density of greater than 0.006 and a degree of ionic character greater than 0.7.
[2] the amount of surfactant corresponds to that giving maximum precipitation of the complex.

This composition gave a wet combing value of 28.

EXAMPLE 7

A clear single-phase hair rinse conditioner with a pH of 7 was made having the following composition.

|  | % |
| --- | --- |
| Poly(acrylic acid) (neutralised with NaOH) | 0.18 |
| Cetyltrimethylammonium bromide[1] | 0.91 |
| Sodium chloride | 2.9 |
| Water | to 100.00 |

[1] the amount of this cationic surfactant is equivalent to 1.0 S where S is the amount of the surfactant to completely neutralise the charge on the anionic polymer.

This composition gave a wet combing value of 30.

EXAMPLE 8

The following clear single-phase hair rinse conditioner was prepared.

|  | % |
| --- | --- |
| Poly(methacrylic acid) | 0.22 |
| Cetyltrimethylammonium bromide | 0.92 |
| Sodium chloride | 3.0 |
| Water | to 100.0 |
| pH adjusted to 7 with NaOH | |

This composition gave a wet combing value of 22.

EXAMPLE 9

The following clear single-phase hair rinse conditioner product was made.

|   | % |
|---|---|
| Merquat 100 | 0.25 |
| Sodium lauryl ether sulphate (3EO) | 0.64 |
| Sodium chloride | 17.0 |
| Propan-1-ol | 3.0 |
| Water | to 100.0 |

The wet combing value for the above product was 25.

EXAMPLE 10

The following clear single-phase hair rinse conditioner product was made.

|   | % |
|---|---|
| Merquat 100 | 0.25 |
| Sodium myristyl sulphonate | 0.48 |
| Ammonium chloride | 10.0 |
| Butyl digol | 8.4 |
| Water | to 100.0 |

This product gave a wet combing value of 30.

For each of the hair conditioners of Examples 1 to 10 the polymer-surfactant complex which separates on dilution of the respective conditioner was present in the diluted product in the form of an hexagonal liquid crystal phase. This phase was observed by examination of samples of the products in a polarising microscope.

EXAMPLE 11

The following clear single-phase hair rinse conditioner was made.

|   | % |
|---|---|
| Merquat 100 | 0.25 |
| Sodium lauryl ether sulphate (3EO) | 0.64 |
| Sodium chloride | 7.7 |
| Ethanol | 25.0 |
| Decanol | 0.75 |
| Water | to 100.0 |

The wet combing value for this product was 30. On dilution the polymer-surfactant complex was deposited as a lamellar liquid crystal phase

COMPARATIVE EXAMPLES A and B

The following clear single-phase hair rinse conditioner products were made.

|   | Comparative Example % | |
|---|---|---|
|   | A | B |
| Merquat 100 | 0.25 | 0.25 |
| Sodium octyl sulphonate | 0.35 | — |
| Sodium lauryl ether sulphate (12EO) | — | 1.27 |
| Sodium chloride | 6.0 | 7.0 |
| Butyl digol | 6.0 | — |
| Water | to 100.0 | to 100.0 |

The wet combing values are given below.

| Product | Wet Combing Value |
|---|---|
| Comparative Example A | 39 |
| Comparative Example B | 40 |

In neither composition A nor composition B does the complex formed between the cationic polymer and the anionic surfactant form a liquid crystal phase. In each of these formulae the amount of the respective surfactant is that required to completely neutralize the charge on the cationic polymer (i.e. S=1).

COMPARATIVE EXAMPLES C and D

In order to further emphasize the importance that the deposited complex be a liquid crystal, the following Comparative Products C and D were prepared which give a polymer-surfactant complex on dilution which is not a liquid crystal. Products C and D were both clear single-phase products.

|   | Comparative Product % | |
|---|---|---|
|   | C | D |
| Polymer QR 686[1] | 0.3 | 0.3 |
| Sodium lauryl ether sulphate (12EO) | 1.8 | — |
| Sodium octyl sulphate | — | 0.51 |
| Sodium chloride | 8.6 | 12.0 |
| Butyl digol | — | 6.2 |
| Water | to 100.0 | to 100.0 |

[1]as in Example 6

Comparative Products C and D gave wet combing values of 46 and 37, respectively. The values are to be compared with the value of 28 obtained with the product of the invention of Example 6 for which the deposited polymer-surfactant complex was in the form of a liquid crystal. In each of Comparative Examples C and D the amount of the respective anionic surfactant was sufficient to completely neutralize the charge on the cationic polymer.

COMPARATIVE EXAMPLES E and F

These are further examples to emphasize that it is important that the deposited polymer-surfactant complex be in the form of a liquid crystal. Whereas in the case of Comparative Examples C and D the failure to produce a liquid crystal was due to an inappropriate selection of the surfactant, in the case of Comparative Examples E and F below, it is due to incorrect choice of the ionic polymer.

|   | Comparative Product % | |
|---|---|---|
|   | E | F |
| MERQUAT 550[1] | 0.25 | — |
| POLYMER JR 400[2] | — | 0.20 |
| Sodium lauryl ether sulphate (3EO) | 0.18 | 0.16 |
| Sodium chloride | 7.00 | 10.00 |
| Water | to 100.00 | to 100.00 |

[1]a cationic copolymer of dimethyldiallylammonium chloride and acrylamide having a charge density of 0.0017 and a degree of ionic character of 0.15; its CTFA designation is Quaternium 41;
[2]a cationic cellulosic derivative as described in U.S. Pat. No. 3 472 840 having a charge density of 0.001 and a degree of inoic character of 0.23; its CTFA designation is Quaternium 19.

Comparative Products E and F were clear single-phase compositions. In each composition the amount of the anionic surfactant was sufficient to completely neutralize the charges on the respective cationic polymer.

Products E and F gave wet combing values of 39 and 43, respectively. Neither of the respective polymer-surfactant complexes which separated on dilution of Comparative Products E and F was in the liquid crystal phase.

EXAMPLE 12

Experiments were carried out to illustrate the effect on the wet combing value of employing amounts of surfactant in excess of that required to completely neutralize the charge on the polymer. The hair treatment composition had the following general formula.

|  | % |
| --- | --- |
| Merquat 100 | 0.25 |
| Sodium lauryl ether sulphate (3EO) | see Table |
| Sodium chloride | 12.0 |
| Propan-1-ol | 2.0 |
| Water | to 100.0 |

TABLE

| Amount of Sodium Lauryl Ether Sulphate | | Wet Combing Value of Composition |
| --- | --- | --- |
| % | S value | |
| 0.65 | 1.0 | 27 |
| 1.3 | 2.0 | 27 |
| 1.63 | 2.5 | 33 |
| 2.67 | 4.1 | 36 |
| 5.85 | 9.0 | 38 |
| 15.0* | 23.1 | 38 |

*This product contained 9.0% sodium chloride rather than 12.0%.

EXAMPLE 13

This example concerns an experiment which shows the importance of the feature of the hair rinse composition of the invention that it is a clear single-phase product, i.e. the polymer-surfactant complex is not present in the undiluted composition as a separate phase.

A complex formed between Merquat 100 and sodium lauryl ether sulphate (3EO) was precipitated in water and collected and then applied directly to wet hair. The amount of the applied polymer-surfactant complex was comparable to the produced on dilution from a single-phase product.

The wet combing value was determined both for the directly applied complex and for the case where the diluted single-phase product was applied. For the former, the wet combing value was 51 compared to a value of 28 for the case where the complex was deposited by dilution of the single-phase product.

COMPARATIVE EXAMPLE G

This example concerns the use of the cationic polymer Merquat 100 in combination with a cationic quaternary ammonium compound. The clear single-phase product had the following composition.

|  | % |
| --- | --- |
| Merquat 100 | 0.25 |
| Cetyltrimethylamonium bromide | 0.57 |
| Water | to 100.0 |

The composition gave a wet combing value of 37.

What is claimed is:

1. An aqueous clear single-phase liquid hair rinse conditioner composition comprising a water-soluble ionized polymer and an ionic surfactant of opposite charge which interact with each other to form a complex which separates out upon dilution of the composition as a lyotropic liquid crystal phase, the composition also comprising an effective amount of a clarifying agent to dissociate or dissolve the complex in order to maintain the composition in the form of a clear single-phase solution prior to dilution, the amount of the ionic surfactant being 0.9 to 2.0S moles where S Moles is the amount of the surfactant required to completely neutralize the charges on the polymer, the combined weight of the ionized polymer and the ionic surfactant being about 0.1 to about 5% by weight of the composition, said composition comprising not more than about 5% by weight of neutral surfactant, and said polymer being selected from the group consisting of poly(methacrylic acid), poly(styrene sulfonate) and copolymers of ethylene and maleic acid.

* * * * *